United States Patent
Zanakis et al.

Patent Number: 5,433,735
Date of Patent: Jul. 18, 1995

[54] ELECTRICAL STIMULATION TECHNIQUE FOR TISSUE REGENERATION

[76] Inventors: Michael F. Zanakis, 67 Smith St., Glen Cove, N.Y. 11542; Philip A. Femano, 69 Alexander Ave., Nutley, N.J. 07110

[21] Appl. No.: 127,055

[22] Filed: Sep. 27, 1993

[51] Int. Cl.⁶ .............................. A61N 1/00
[52] U.S. Cl. ............................ 607/50; 607/116
[58] Field of Search .......... 607/50, 51, 75, 115, 607/116; 128/897, 898; 623/15

[56] References Cited

U.S. PATENT DOCUMENTS

| | | | |
|---|---|---|---|
| 3,842,841 | 10/1974 | Brighton et al. | 607/75 X |
| 4,019,510 | 4/1977 | Ellis | 607/50 X |
| 4,461,300 | 7/1984 | Christensen | 607/51 X |
| 4,846,181 | 7/1989 | Miller | 607/50 |
| 4,919,138 | 4/1990 | Nortenstroöm | 607/50 |
| 5,158,081 | 10/1992 | McWhorter et al. | 607/50 |

FOREIGN PATENT DOCUMENTS 1110455  8/1984  U.S.S.R. .............................. 607/50

OTHER PUBLICATIONS

Stan et al., *Electric Stimulation of Bone Growth & Repair*, "Effect of Direct Current on the Healing of Fractures", pp. 47-53, 1978.

*Primary Examiner*—Lee S. Cohen
*Assistant Examiner*—Jeffrey R. Jastrzab
*Attorney, Agent, or Firm*—Michael Ebert

[57] ABSTRACT

Regeneration of damaged tissue, whether in the skin, tendons or elsewhere in the body begins with the growth and proliferation of cells which take place along a migratory path and in a polar direction that depends on the nature of the injury. Thus in some situations, regenerative cells and non-cellular healing components migrate radially from the outskirts of the damaged tissue region toward the center thereof, while in others migration is along a longitudinal or transverse path. To stimulate and enhance this regenerative process and thereby promote rapid healing of the damaged tissue, use is made of an exogenous electrical stimulation technique in which cathode and anode electrodes are placed in or near the region. Impressed across the electrodes is a DC potential whose magnitude is sufficient to cause a minute ionic and electronic current to flow between the electrodes through the region. The electrodes are so shaped and oriented relative to the region that the resultant current flow is substantially along the same path followed by the migrating cells in the course of the regenerative process and in a polar direction conducive to healing.

8 Claims, 2 Drawing Sheets

ELECTRICAL STIMULATION TECHNIQUE FOR TISSUE REGENERATION

BACKGROUND OF INVENTION

1. Field of Invention

This invention relates generally to electrotherapy, and more particularly to an electrical stimulation technique and apparatus therefore for conducting a direct-current through the skin, or through tendons and ligaments or other damaged tissue in order to facilitate the regeneration thereof as well as to promote blood reperfusion in damaged tissue, such as in nerves.

2. Status of Prior Art

Electrical currents passing through a biologic system can give rise to thermal, physiochemical and physiologic effects. It is now recognized that electrical currents applied to damaged tissue may be conducive to tissue growth and repair. In applying these currents, various techniques have heretofore been used, such as surgical implantation of current-delivering electrodes.

It is well known in electrotherapy that one can promote healing of damaged tissue by subjecting the tissue to an electromagnetic field produced by inductive coupling means, or to an electrostatic field created by capacitive coupling means. In conradistinction, the present invention resides in an exogenous electrical stimulation technique in which electrodes are placed within or near the damaged tissue region to cause, when a DC potential is impressed across the electrodes, an ionic and electronic current to flow through the tissue region being treated. The magnitude of this potential is usually about 1.5 volts to avoid electrolysis and the resultant release of gas, the current flowing through the tissue region being in the milliampere or microampere range.

A detailed disclosure of various electrical stimulation techniques can be found in the article by Black entitled "Electrical Stimulation of Hard and Soft Tissue in Animal Models," which appears in Plastic Surgery, Vol. 12, No. 2, Apr. 25, 1985.

In stimulating wounded tissue with an electrical current, the healing modes are generally of two kinds, primary and secondary. In primary repair, the damaged tissues are left in their original positions or are reapproximated, and they are caused to heal by a renewal of cells at the site of injury. In secondary repair, the tissues are not reapproximated, and in many cases will exhibit a gap where a portion of the tissue has been excised. In an early cell growth and proliferation stage, this gap is bridged by a granulation bed which remodels and matures into a fibrous scar. A "wound module" is created which is a complex of tissues and cell populations that migrate into the wound from the edges of the lesion. Successive stages of coagulation, inflammation tissue elaboration and remodeling occur. Artificial intervention by electrical stimulation serves to accelerate any or all of these phases.

The cellular events which take place in the course of regenerating damaged living tissue are described in detail in the chapter entitled "The Physiology of Wound Healing" included in the text "Wound Healing and Wound Infection" by T. K. Hunt; Appleton-Century Crafts—1980.

When most tissues are traumatized, an "injury current" is produced, which is positive relative to the surrounding tissue. In biological tissues, current is carried by ions, not electrons; hence the injury current is an ionic current flowing in the direction in which positive ions (cations) move. When cells and tissues are damaged, ions "leak" from their compartmentalized and charge-separated medium to the immediate environment.

The skin, for example, acts as a membrane with an internal positive charge. In damaged skin, there is a steady injury current which is driven outward, so that there is an external positivity with respect to the adjacent uninjured areas. Although there is inadequate evidence to support the hypothesis that electrical currents flowing through the damaged tissue can alter the injury current, it is not unreasonable to assume that it does have an effect. Moreover, there may be additional cellular mechanisms only peripherally related to the injury current upon which applied electric currents exert their influence.

The regeneration of damaged body parts in a skin wound healing process commences with the growth and proliferation of cells. The tissues having the greatest capacity for repair are generally those subject to the greatest chance of traumas such as bone, cartilage, tendon, muscle, skin, blood vessels, peripheral nerves and mucose. Most methods heretofore developed to enhance the natural healing process involve some kind of pharmacological intervention, although medical devices such as sutures and staples are commonly used in surgical practice. Other methodologies are somewhere in between. An example is the use of exogenously applied electrical fields which can serve to alter the course of tissue response to injury. The electrical fileds can be applied in an alternating-current (AC) manner or in a direct-current (DC) manner, either in a steady state or in a pulsed mode.

The references listed below discuss various exogenous electrical signal techniques for stimulating the regeneration and repair of damaged tissue.

1. Bassett, C. A. L., Mitchell, S. N. and Gaston, S. R. Treatment of ununited tibial diaphyseal fractures with pulsing electromagnetic fields. J. Bone and Joint Surgery. 63A:511, 1981.

2. Brighton, C. T., Friedenberg, Z. B., Mitchell, E. I., and Booth, R. E. Treatment of nonunions with constant direct current Clin. Orthop. Relat. Research 124:106, 1977.

3. Assimacopoulos, D. Wound healing promotion by the use of negative electric current. Am. Surgeon. 34:423, 1968.

4. Bigelow, J. B., Al-Husseini, S. A., Von Recum, A. F. and Park, J. B. Effect of electrical stimulation of canine skin and percutaneous device—skin interface healing in D. T. Brighton, J. Black and S. R. Pollack (eds.), Electrical properties of Bone and Cartilage: Experimental Effects and Clinical Applications. N. Y. Grund and Stratton 1979, p. 289.

5. Konikoff, J. J. Electrical promotion of soft tissue repairs. Ann. Biomed. Engineering 4:1, 1976.

6. Brummer, S. B. and Roblee, L. S. Criteria for selecting electrodes for electrical stimulation: theoretical and prectical considerations. Ann. N. Y. Acad. Sciences 405:159, 1983.

7. Laub, F. and Korenstein, R. Actin polymerization induced by pulsed electric stimulation of bone cells in vitro. Biochem, Biophys. Acts. 803:308, 1984.

8. Korenstein, R., Somjen, D., Fischler, D. and Binderman, I. Capacitive pulsed electric stimulation of bone cells; induction of cyclic-AMP changes and DNA systhesis. Biochem. Biophys. Acta. 803:302, 1984.

9. Roden, G. A., Bourret, L. A. and Norton, L. A. DNA synthesis in cartilage cells is stimulated by oscillating electric fields. Science 199:690, 1978.

10. Roley, B. A., McKenna, J. M., Chase, G. R. and Wolcott, L. E. The influence of electrical current on an infecting microorganism in wounds. Ann. N. Y. Acad. Sciences 238:543, 1974.

11. Wolcott, L. E., Wheeler, P. C., Harwicke, H. N. and Rowley, B. A. Accelerated healing of skin ulcers by electro-therapy: preliminary clinical results S. Med. J. 62:795, 1969.

SUMMARY OF INVENTION

The main object of this invention is to provide an electrical stimulation technique and apparatus therefore adapted to promote the regeneration and healing of living tissue that is more effective than electrical stimulation techniques heretofore used for this purpose.

More particularly, an object of this invention is to provide an electrical stimulation technique and apparatus therefor in which a direct current passing through the tissue region to be treated accelerates the healing of injured skin, tendons, ligaments, blood vessels, and other soft tissues and promotes blood perfusion in the tissues.

A significant feature of the invention resides in anode and cathode electrodes which are so shaped and oriented relative to the tissue region to be treated as to produce when a voltage is applied across the electrodes an ionic and electronic current flow through tissue that travels in a path therein and in a polar direction serving to accelerate the regenerative healing process. In some situations, however, as in the treatment of a cancerous tumor, the polar direction is reversed to inhibit cell growth and proliferation in the tumor.

Yet another object of the invention is to provide electrodes that can readily be shaped and oriented with respect to a tissue region to be treated.

Also an object of this invention is to provide electrodes for use in an electrical stimulation technique to promote wound healing that can be implanted in the tissue region to be treated and can be readily withdrawn therefrom after healing is completed without injury to the healed tissue.

Briefly stated, this invention is based on the recognition that regeneration of damaged tissue, whether in the skin, tendons or elsewhere in the body begin with the growth and proliferation of cells which take place along a migratory path and in a polar direction that depends on the nature of the injury. Thus in some situations, regenerative cells and non-cellular healing components migrate radially from the outskirts of the damaged tissue region toward the center thereof, while in others migration is along a longitudinal or transverse path.

To stimulate and enhance this regenerative activity and thereby promote rapid healing of the damaged tissue region, use is made of an exogenous electrical stimulation technique in which cathode and anode electrodes are placed in or near the region. Impressed across the electrodes is a DC potential whose magnitude is sufficient to cause a minute ionic and electronic current to flow between the electrodes through the region. The electrodes are so shaped and oriented relative to the region that the resultant current flow is substantially along the same path followed by the migrating cells in the course of the regenerative process and in a polar direction conducive to healing.

BRIEF DESCRIPTION OF DRAWINGS

For a better understanding of the invention, as well as other objects and further features thereof, reference is made to the following detailed description to be read in conjunction with the accompanying drawings, wherein.

DESCRIPTION OF INVENTION

Figure 1:
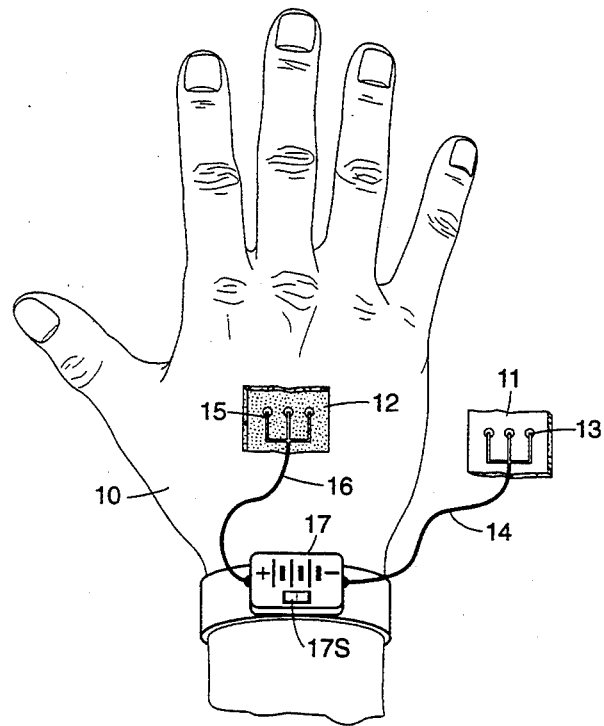
FIG. 1 schematically illustrates an electrical technique in accordance with the invention as applied to a skin graft and the electrode configuration appropriate thereto.

The present invention is based on our discovery that healing of damaged living tissue by electrical stimulation can be significantly improved by passing a direct ionic and electronic current through the tissue region being treated in a predetermined path and in a polar direction along the path that is appropriate to the nature of the injury and is conducive to the natural healing process.

As used herein, the term "path" refers to a passage extending between separated first and second poles. By "polar direction" is meant the direction taken by current flow or cell migration along this path, which is either from the first pole to the second, this being the forward direction, or from the second pole to the first, this being the reverse direction. The current flow direction depends on the polarity of the voltage applied to the electrodes, and when the voltage applied to a given electrode is negative, the electrode then acts as a cathode from which current flows toward the other electrode which is then the anode. Reversal of the applied polarity results in a reversal of polar direction.

It is well established that regeneration of damaged living tissue, whether in the skin, tendons, ligaments, blood vessels or elsewhere in the body, commences with the growth and/or proliferation of cells. As this activity proceeds in the healing process, a gradual migration takes place of the regenerative cells and non-cellular healing components which accompany the cells along a path and in a polar direction which depends on the nature of the tissue injury. Hence when the injury takes the form of a deep cut, a lesion, a laceration or other type of tissue damage, it is the character of the injury that determines the migratory path and polar direction of the regenerative cells.

Thus in some instances, the regenerative cells as well as the non-cellular components will in the course of the healing process orient themselves and migrate radially inward from the outskirts of the damaged tissue region toward its center or core. In other cases, orientation and migration may be along a transverse or longitudinal path in a particular polar direction.

In our electrical stimulation technique, a direct potential is applied across anode and cathode electrodes placed in or near the damaged tissue region to be treated. The magnitude of this potential is sufficient to cause a minute ionic and electronic current to flow continuously between the electrodes in the milliampere or microampere range. We have discovered that when these electrodes are so shaped and oriented as to cause this current to flow continuously through the tissue in substantially the same path taken by the migrating cells in the course of tissue regeneration, the resultant interaction stimulates and accelerates the regenerative process and promotes rapid healing of the damaged tissue. In some instances, the flow may be made discontinuous.

In most situations, our electrical stimulation technique works best when the polar direction of electronic current flow through the tissue along the cell migratory and orientation path is in the same polar direction as that taken by the migratory cells and the extracellular components which accompany these cells to effect healing. But in some situations, as in the treatment of cancerous tumors, best results are realized when the current flow is in the reverse polar direction with respect to the migratory cell movement and alignment along the same or substantially the same path.

The cytoarchitecture of damaged tissue mandates that the cells and extracellular components align themselves in a particular fashion in order to recover their pre-damage orientation such as in a straight line or in stacks. In an electrical stimulation technique in accordance with the invention, the ionic and electronic current exerts a trophic influence on cellular orientation to facilitate the development of a cytoarchitecture appropriate to the damaged tissue undergoing repair.

As applied to the repair of a damaged tissue region on the skin, such as a skin graft, we have found that placement of the anode electrode on the dorsal or outer skin surface and placement of the cathode electrode under the skin is the most effective arrangement. Thus the resultant current flow between the electrodes serves to stimulate the cells and the accompanying extracellular components to stack themselves.

With regard to reperfusion by vasculature, several related events may be trophically influenced by the electrical stimulation technique. In reperfusion by vasculogenesis or angiogenesis, epithelial cells need to align themselves in an almost linear fashion. Cell orientation and migration play a key role in the process of angiogenesis, and this process is significantly enhanced by trophically inducing proper cell alignment. In reperfusion by opening up of previously closed vessels, epithelial integrity can be enhanced by proper electrical stimulation in which the ionic and electronic current flow extends not only through epithelial cells but also to the outer layers of the vessels to treat the connective tissue and the musculature of the vessel wall.

Tendon and ligament repair also involve the migration of cells and extracellular components from the outskirts of the damaged tissue region to be treated to the core of the damaged tissue. Once in the vicinity of the damage, the cells and extracellular components align themselves along the length of the tissue, thereby enabling the application of maximum force thereto when the tissue is fully healed.

In all instances, in an electrical stimulation technique in accordance with the invention, the path taken by the ionic and electronic current and its polar direction along this path are such as to facilitate proper orientation of the cells and the extracellular components.

Skin Defects Requiring a Graft:

The electrical stimulation apparatus in accordance with the invention shown in FIG. 1 is applicable to those situations where a region on the skin is so damaged as to require a graft to effect repair, such as a region on the skin of the hand 10.

To effect such repair, a generally rectangular graft 11 is provided which is dimensioned to seat within a complementary cavity 12 formed by excising the damaged skin region, the graft having substantially the same thickness as the skin. Secured topically to the surface of skin graft 11 is an electrode formed by an array of fine wires 13 joined to a common lead 14. Seated within cavity 12 to engage the undersurface of the graft is a similar electrode array 15 joined to a common lead 16.

Lead 14 and 16 are connected to the positive and negative terminals of a compact battery pack 17. In practice, this pack is strapped onto the wrist of the hand, as shown in FIG. 1. Alternatively, battery pack 17 can be carried elsewhere on the body of the patient being treated, or it may be implanted under the skin.

Figure 2:
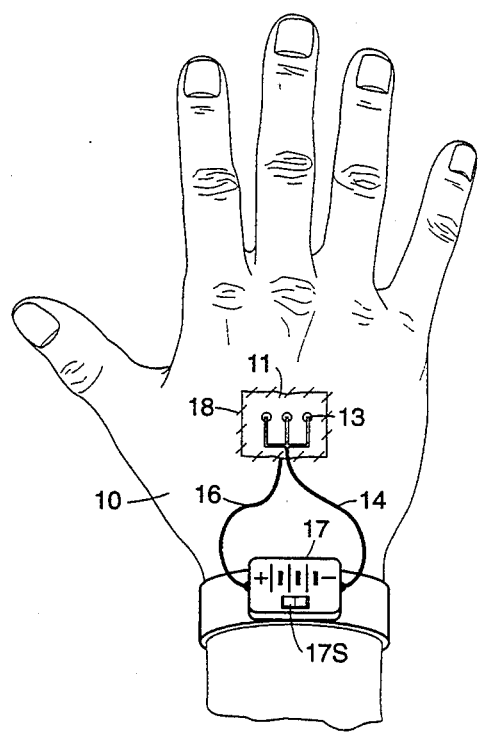
FIG. 2 shows the graft in place in the skin so that an ionic and electronic current may be caused to flow through the graft to promote its integration with the surrounding skin.

As shown in FIG. 2, skin graft 11, after being seated in the cavity, is sewn by a suture 18 to the surrounding skin on hand 10 so that now the healing process can proceed.

In a regenerative situation of this type, cell growth and proliferation give rise to the migration of cells and non-cellular healing components in a migratory path normal to the plane of the graft. The path of the ionic and electronic current which flows through the graft between electrodes 13 and 15 positioned on opposite face of the graft is substantially along the same path. The reason for an array of electrodes spread over the outer and inner faces of the graft is to distribute current flow throughout the body of the graft.

More efficacious results are usually obtained when electrode 15 under the graft acts as the cathode; hence this electrode is connected to the negative terminal of power pack 17, while electrode 13 on the outer face of the graft then acts as the anode and is connected to the positive terminal.

We have found, however, that in some situations a reverse polar direction of current flow is as effective or more effective than a forward polar direction of current flow in promoting the regenerative process. Hence DC power pack 17 is provided with a polarity-reversing switch 17S. In a given situation in which the negative and positive terminals of the power pack are connected to the electrodes of the electrical stimulation apparatus, an operator, simply by actuating switch 17S, can reverse the polar direction. But in all instances, regardless of the selected polar direction, the electrodes must be so shaped and oriented with respect to the region of damaged tissue being treated as to cause the resultant ionic and electronic current to flow in a path which is substantially the same as the migratory cell path, the latter being predetermined by the nature of the injury.

The wires in the array which form electrodes 13 and 15 and leads 14 and 16 therefor are very fine and thread-like in nature, thereby making it possible, after healing has been completed, to cleanly, and without encountering resistance, pull out the electrode wires from the tissue site. And while this withdrawal action leaves fine tunnels in the tissue site, these are quickly healed.

Figure 3:
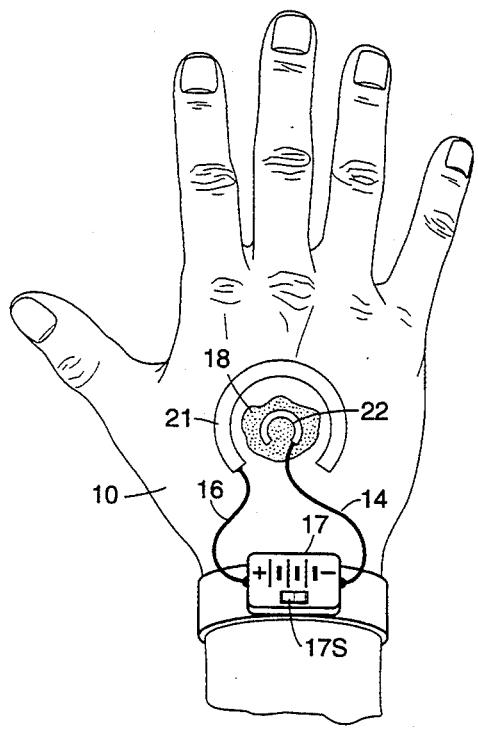
FIG. 3 shows a shapable electrode tape in accordance with the invention.

Electrode Tapes:

FIG. 3 illustrates a hand having on its skin a large lesion 18, such as a burn, the nature of which is such that the proper treatment is not a grafting operation but regeneration, in situ of the damaged tissue.

In this situation, the regenerative process involves the growth and proliferation of cells which are accompanied by non-cellular components and migrate from the skin area surrounding the damaged tissue region in radial paths leading inwardly toward the core or center of the region.

It is necessary, therefore, in order to provide an electrical stimulation technique appropriate to this situation to shape and orient the electrodes to which a DC potential is applied to produce a continuous ionic and electronic current that flows along the same radial paths taken by the migrating cells.

Figure 4:
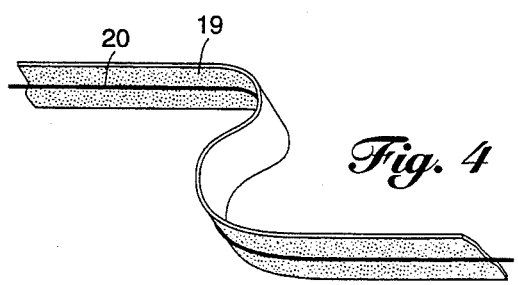
FIG. 4 shows the shapable electrode tape in the form it assumes when applied to a damaged tissue region on the hand.

To provide electrodes that can be made to assume any desired shape and which can be temporarily attached to the skin at a desired orientation with respect to the damaged tissue region, the electrodes are derived from an electrode tape, as shown in FIG. 4. Tape 19 is of flexible, porous fabric or plastic material or any other tape material suitable for use as medical adhesive tape. Bonded to the adhesive face of tape 19 is a fine bare wire 20 which runs along the central longitudinal axis of the tape.

Two sections 21 and 22 of different length are cut from the electrode adhesive tape which may be stored in roll form. These electrodes are applied, as shown in FIG. 3, to the surface of the skin and adhered thereto to create concentric electrodes. Electrode tape section 21 is shaped into a large outer ring which surrounds the lesion region 18, while the shorter section 22 is shaped to form of ring of much smaller diameter, this ring being placed at the center or core of the lesion region.

The electrode tape section 21 and 22 are connected by leads 14 and 16 to the DC power pack 17. The resultant ionic and electronic current which flows through lesion region 18 travels in radial paths which substantially correspond to the radial paths taken by the migrating cells. We have found that best results are obtained when the polar direction of flow is from inner electrode section 22, acting as a cathode, toward outer electrode section 21 acting as an anode.

Because the adhesive tape electrode shown in FIG. 4 may be adhered to the skin to assume any desired configuration at any desired position, this tape is useful in an electrical technique in accordance with the invention which requires shaping and orientation of the electrodes to produce a current flow along a path which is substantially the same as the path taken by the migrating cells in the regenerative process.

Figure 5:
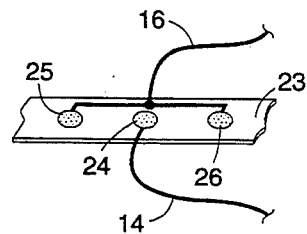
FIG. 5 illustrates an electrode bandage in accordance with the invention.

Electrode Bandage:

For small lacerations, use may be made of an adhesive electrode bandage, as shown in FIG. 5, in which the adhesive face of bandage 23 has bonded thereto a center pole 24 and two outer poles 25 and 26 on either side of the center pole. In practice, the center pole is connected to lead 14 and the interconnected outer poles 25 and 26 are connected to lead 16. This bandage is applied to the laceration so that center pole 24 is at the core of the laceration and outer poles 25 and 26 are just outside the laceration on either side of its core. In practice, the bandage may incorporate a power supply in the form of a flexible ribbon type battery secured to the bandage proper.

Hence in this situation, the ionic and electronic current paths extend from the center of the laceration laterally to the outer poles. This current path substantially corresponds to the path taken by the migratory cells in the course of the regenerative process. The polar direction of current flow is preferably from the center pole, acting as a cathode, toward the anodic outer poles. However, in some instances good results may be obtained by reversing the polar direction. One can determine empirically which polar direction is most effective.

Electrode Sutures:

In some situations, suturing is the appropriate methodology, and it is then necessary, using the electrical stimulation technique, to promote healing of the sutured region. To this end, an electrode suture is provided in which the suture functions not only as a ligature but also as the anode and cathode of the electrical stimulation apparatus.

Figure 6:
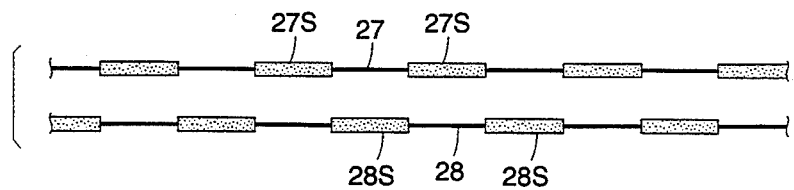
FIG. 6 separately shows the two components of an electrode suture in accordance with the invention.
Figure 7:
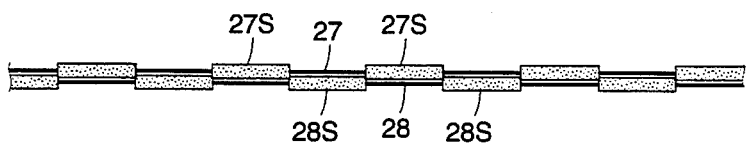
FIG. 7 shows the components when combined to create the electrode suture.

As shown in FIG. 6, the electrode suture is composed of conductive fine wires or threads 27 and 28. Thread 27 is provided at equi-spaced positions with thin insulation sleeves 27S of flexible plastic material, such as polyvinyl or polypropylene which is medically sterile and inert. The length of each sleeve is equal to the length of the uninsulated thread section between sleeves. Thread 28 is provided at positions which are staggered with respect to the sleeves on thread 27 with insulation sleeves 28S. The two threads whose insulation sleeves are formed of thermoplastic material are bonded together, as shown in FIG. 7, so that each sleeve on one thread is joined to the uninsulated section on the other thread, the two threads thereby being integrated into a sewable composite suture.

Figure 8:
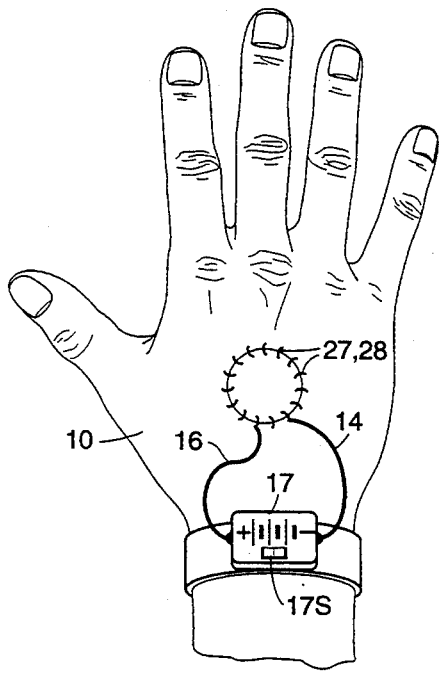
FIG. 8 shows the electrode suture sewn to an injured tissue region of the hand.

When, as shown in FIG. 8, a skin area is sutured by the electrode suture and conductive threads 27 and 28 of the suture are connected by leads to DC power pack 17, then a potential is applied across these threads, one of which functions as an anode of the electrical stimulation apparatus and the other as the cathode, depending on the polarity of the applied potential.

Figure 9:
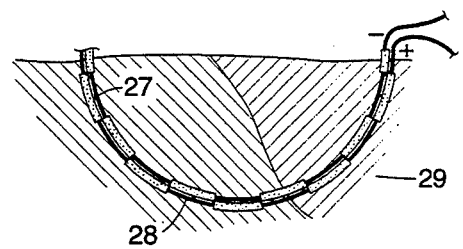
FIG. 9 shows, in section, a loop of the electrode suture implanted in the skin.

As shown in FIG. 9, when skin 29 is penetrated by the suture, an ionic and electronic current will flow between the staggered exposed conductive sections of threads 27 and 28 in paths in the tissue region surrounding the suture that are substantially the same as the paths taken by the migrating regenerative cells in that region.

In practice, the suturing may be so sewn that the uninsulated sections of one conductive thread are just above the skin surface in contact therewith and the uninsulated sections of the other thread are embedded in the skin.

When the threads of the composite suture are composed of fine metal wires having insulation sleeves thereon at equi-spaced positions, then after healing has been completed it is necessary to cut and withdraw the threads, as with a conventional suture. But by making the composite suture of biodegradable material of the type used in sutures which are gradually absorbed by the tissue, the biodegradable material, though non-metallic, being rendered conductive by Aquadag or similar particles dispersed in the material, then no need exists to cut and withdraw the suture after healing is completed.
Reperfusion:

For injuries requiring reperfusion, the appropriate electrode system for the electrical stimulation technique will depend largely on the application of interest.

Figure 10:
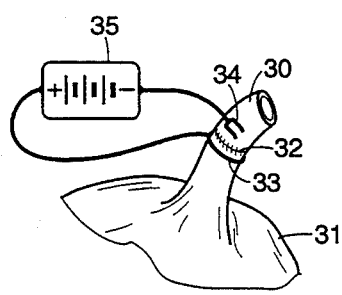
FIG. 10 illustrates a coronary artery provided with the electrode suture.

Thus to facilitate perfusion of heart bypass grafts by angiogenesis, where, as shown in FIG. 10, a large vein or coronary artery 30 is joined to the heart 31 by a suture 32, then surrounding artery 30 adjacent the suture is a ring electrode 33. Inserted in the lumen of the artery is an electrode 34 formed by thread-like wires that can be withdrawn after healing is completed.

Electrode 34 and electrode 33 are connected by leads to a DC power supply 35. A similar electrode configuration may be used in the anastomosis of large vessels as well. Also, the electrode may be run through the vein or artery to a large, peripheral vessel similar to a catheter for later retrieval.

In muscle grafting and reperfusion, an electrode system of the above described type may also be used. It is to be noted that electrical stimulation has been reported to reduce thrombus formation.

Gastrointestinal Tract:

Repair of the gastrointestinal track presents special problems. For example, reanastomosis following excision of part of the colon may be performed using the electrode suture technique previously described to promote healing by the electrical stimulation technique.

Figure 11:
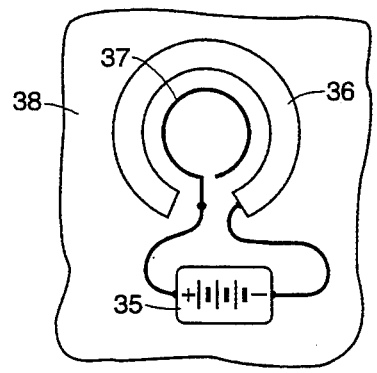
FIG. 11 illustrates the electrode arrangement for creating an ostomy.

In the creation of an ostomy to the outside of the body wall, it is efficacious to apply a tape electrode 36 in a ring formation, as shown in FIG. 11, to the outside skin 38, this tape electrode being of the type shown in FIG. 4, and to apply an inner wire ring 37 to the inner portion of the stomach.

In surgical procedures the use of stapling rather than filamentary sutures is now commonplace, the staples bridging an incision so that the teeth of each staple stradles the incision. To promote healing by electrical stimulation, anodal current can be applied to the teeth of the staples and cathodal current to the yoke joining the teeth, in which case the yoke must be insulated from the teeth. Or in a series of staples inserted along an incision, a positive potential could be applied to the even numbered staples in the series and a negative potential to the odd numbered staples.

It is important to bear in mind that in an electrical stimulation technique in accordance with the invention, it is essential that the shape of the cathode and anode electrodes and their orientation with respect to the tissue region being treated by such as to produce an ionic and electronic current which flows in a path substantially following the path to be taken by cell migration, this migrating path being predetermined by the nature of the tissue injury.

In reperfusion of a vessel we have found that electrical stimulation in a direction appropriate to the migratory path taken by the cells also acts to promote blood flow or reperfusion through the stimulated tissues. And in lieu of an electrode bandage in which electrodes are attached to tape, the electrodes can be applied to a gauze or other surgical covering.

Whether the polar direction of current flow in the path is forward or reverse, it must be such as to facilitate the regeneration of cells in the healing process. Usually, a forward polar direction of current flow which correspondes to the polar direction of cell migration is most conducive to the regenerative process, though in some instances a reverse polar direction is more effective. Specific combinations of skin healing and reperfusion or reperfusion and tendon healing may necessitate electrode shapes and orientations which act to maximize each response. Thus when it is important for skin to be reperfused, skin cell migration is also needed.

There are, however, special situations in which it is desirable to inhibit or retard the growth and proliferation of cells, as in carcinogenic tumors. In that situation, the electrical stimulation technique in accordance with the invention can be used to produce a current flow through the tumor which is along the same path at which proliferating tumor cells seek to migrate, but the polar direction of the current is then the reverse of the polar direction taken by the migrating cells so as to inhibit such migrations.

While there have been shown preferred embodiments of an electrical stimulation technique for stimulating tissue regeneration in accordance with the invention, it will be appreciated that many changes and modifications may be made therein without, however, departing from the essential spirit thereof.

We claim:

1. An electrical technique for stimulating a natural process of regenerating damaged living tissue resulting from an injury which begins in a region of the damaged tissue with growth and proliferation of cells and their migration accompanied by non-cellular components along a migratory path determined by the nature of the injury, said technique comprising the steps of:
   (a) determining a direction of the migratory path in the region of the damaged tissue;
   (b) placing adjacent the region of the damaged tissue to be treated removable cathode and anode electrodes;
   (c) shaping and orienting said electrodes with respect to the region of damaged tissue, and
   (d) impressing across the electrodes a DC potential having a magnitude sufficient to cause an ionic electronic current to flow through the tissue region, such that said current is caused to flow along substantially the same path taken by the migration of cells in the course of tissue regeneration and in a polar direction conducive to healing.

2. A technique as set forth in claim 1, wherein said current is in a milliampere to microampere range in which electrolysis does not occur in the damaged tissue.

3. A technique as set forth in claim 1, wherein said polar direction is in the same polar direction as that taken by the migration of cells.

4. A technique as set forth in claim 1, wherein said polar direction is in a direction that is the reverse of that taken by the migration of cells.

5. A technique as set forth in claim 1, wherein the placing step comprises applying one of said electrodes below graft seated in a cavity formed in the skin and placing the other on the surface of the graft.

6. A technique including the steps set forth in claim 1, wherein said placing step comprises placing an array of fine thread-like wires connected to a common lead adjacent the region of the damaged tissue, said wires being withdrawable from the tissue after healing is complete.

7. A technique as set forth in claim 1, wherein said damaged tissue is a skin lesion region, and wherein said shaping step comprises shaping one of said electrodes into a large ring, placing said ring to surround the region, shaping the other electrode being shaped into a small ring, and placing said other electrode to lie at the center of the region.

8. An electrical stimulator technique as set forth in claim 1 wherein said placing step comprises placing said electrodes adjacent a carcinogenic tumor so as to inhibit the growth and proliferation of cells which seek to migrate in a predetermined path, and applying said DC potential to said electrodes to cause an ionic and electronic current to flow through the tumor in substantially the same path and in a polar direction opposed to the polar direction taken by the cells along the migratory path.

* * * * *